US006643007B2

(12) United States Patent
Le

(10) Patent No.: US 6,643,007 B2
(45) Date of Patent: Nov. 4, 2003

(54) APPARATUS FOR OPTICAL INSPECTION OF A WORKING SURFACE HAVING A DYNAMIC REFLECTIVE SPATIAL ATTENUATOR

(76) Inventor: Tuan Le, 15218 E. Riviera La., La Mirada, CA (US) 90638

( * ) Notice: Subject to any disclaimer, the term of this patent is extended or adjusted under 35 U.S.C. 154(b) by 0 days.

(21) Appl. No.: 09/905,839

(22) Filed: Jul. 13, 2001

(65) Prior Publication Data

US 2002/0044278 A1 Apr. 18, 2002

Related U.S. Application Data

(60) Provisional application No. 60/217,568, filed on Jul. 12, 2000.

(51) Int. Cl.[7] .............................................. G01N 21/00
(52) U.S. Cl. ............................. 356/237.3; 356/237.2; 356/237.4
(58) Field of Search ........................ 356/237.3, 237.2, 356/237.4

(56) References Cited

U.S. PATENT DOCUMENTS

| 5,276,498 A | 1/1994 | Galbraith et al. ............ 356/237 |
| 5,506,676 A | 4/1996 | Hendler et al. ............. 356/237 |
| 5,519,206 A | 5/1996 | Uwira ....................... 250/208.1 |
| 5,629,768 A | 5/1997 | Hagiwara ................... 356/237 |
| 5,742,422 A | 4/1998 | Drake ........................ 359/227 |
| 5,966,212 A | 10/1999 | Hendler et al. ........... 356/239.3 |
| 6,003,993 A | 12/1999 | Webb ......................... 351/221 |
| 6,392,794 B1 * | 5/2002 | Engelhardt et al. ......... 359/368 |
| 6,411,349 B2 * | 6/2002 | Nakazawa et al. ........... 349/42 |

FOREIGN PATENT DOCUMENTS

JP           411231249 A  *  8/1999

OTHER PUBLICATIONS

By David Leith "Light Scattering Theory", Particle Control for Semiconductor Manufacturing. 1990, pp. 47–59.

* cited by examiner

Primary Examiner—Jordan M. Schwartz
Assistant Examiner—Tim Thompson
(74) Attorney, Agent, or Firm—Liu & Liu

(57) ABSTRACT

A dynamic reflective spatial attenuator for use in an optical inspection apparatus. The attenuator takes the form of a two-dimensional micro-mechanical reflective array that, in the first operative position of a mirror element, reflects the desired scattered light toward a detector and, in the second operative position of a mirror element, reflects undesired scattered light into a light dump. The mirror array's fast response and flexibility allows for changes during mid-scan to increase the defect's or contaminant's signal relative to the substrate surface's signal.

25 Claims, 6 Drawing Sheets

Collection Angle vs. Incidence Beam

Collection Angle vs. Substrate Surface

Fourier Diffraction Pattern Filter

Light Attenuation 1/3 (40) vs. 2/3 (42)

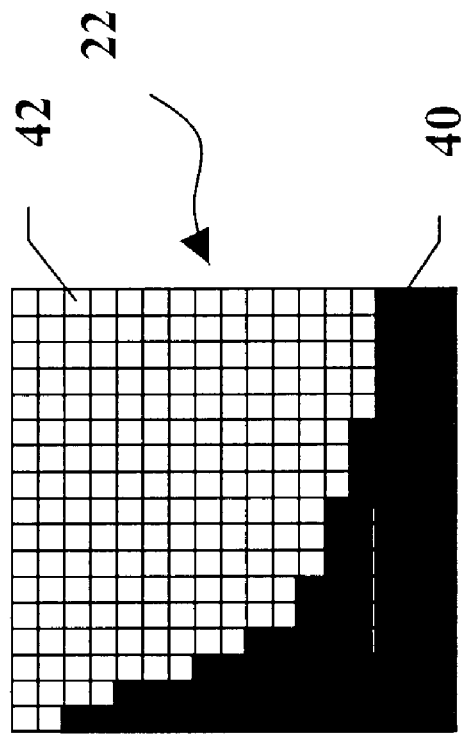
FIG 3F
Collection Angle vs.
Incidence Beam
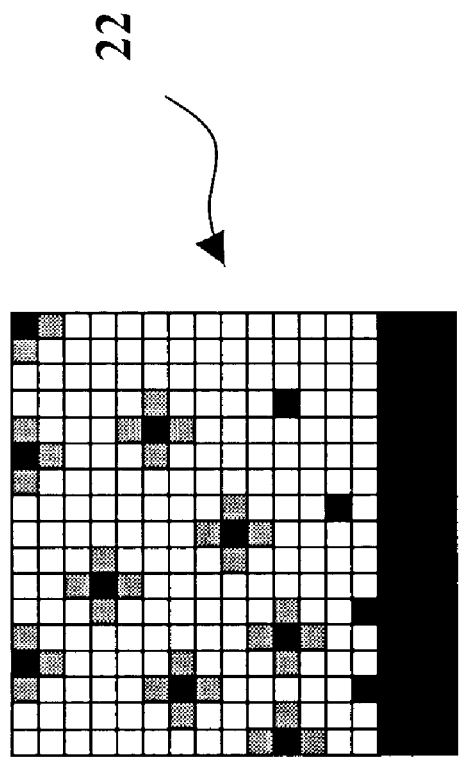
FIG 3E
Two Filtration Patterns
Superimposed: FIG 3A &
FIG 3C

APPARATUS FOR OPTICAL INSPECTION OF A WORKING SURFACE HAVING A DYNAMIC REFLECTIVE SPATIAL ATTENUATOR This is a continuation-in-part application of earlier application No. 60/217,568, filed Jul. 12, 2000.

BACKGROUND OF THE INVENTION

1. Field of the Invention

The present invention relates to an inspection apparatus for optically inspecting working surfaces, and more particularly to an optical inspection apparatus having a dynamic spatial attenuator.

2. Description of Related Art

The silicon manufacturing process requires a pure environment free from contaminants that often produce undesired and unexpected effects on device performance. These effects can range from damaged photomasks to unwanted electrical properties in the case of semiconductor chips, and from physical obstructions to weakened mechanical properties in the case of nanofabricated machinery. Maintaining a pure manufacturing environment requires the detection of such contaminants on the device surface before their elimination can begin.

Most contaminants on the device surface are too small to be seen by the naked eye. Hence, one approach to detect them is to use an inspection apparatus that illuminates the substrate's surface with a laser beam. If a contaminant exists on the substrate's surface, it will scatter light in all directions. The intensity of the scattered light depends on a number of variables, such as the contaminant's size, the contaminant's and the substrate's refractive index, the illumination angle, the collection angle, and the illumination source's wavelength and intensity. Photo-detectors strategically placed around the hemisphere above the substrate will detect the scattered light and convert it into an electrical signal for further analysis and classification. Inspection of an unpatterned substrate with such an apparatus is simple because the electrical signal is constant if the unpatterned substrate is clean and free of irregularity. Conversely, any sharp deviation in the electrical signal's amplitude may be attributed to an undesired surface condition such as the presence of a contaminant, surface defect, or other irregularity on the surface that causes an interruption in the pattern of the scattered light. Further attention would be required to determine the nature of the surface condition and to identify whether it is defect related.

Inspecting a patterned substrate is more complex than inspecting an unpatterned substrate because scattered light produced by the pattern's topography is mixed in with light scattered by a possible contaminant, defect or other undesired surface conditions. Most signals produced by the patterns, however, are periodic and can be filtered out by computer hardware or software, leaving behind the non-periodic signals for further analysis. If the periodic features are much smaller than the spot size of the illumination laser beam (i.e., an array of cells in a memory area), these features will behave like a reflective diffraction grating and produce a Fourier diffraction pattern. One method to remove this Fourier diffraction pattern, thus enhancing the contaminant or defect's signal vis-à-vis the Fourier diffraction pattern's signal, is to employ a Fourier transform lens to focus the diffraction pattern onto a spatial filter located on the Fourier transform plane.

Several methods of filtering this Fourier diffraction pattern exist in the art. One method uses a spatial filter comprised of a planar array of individually addressable light valves using transparent liquid crystal technology (see, U.S. Pat. No. 5,276,498 to Galbraith et al.). Technology based on transparent liquid crystal is inefficient when compared to reflective mirrors due to the material's opaqueness. A second method uses a photographic plate to capture the Fourier diffraction pattern and translate the photographic negative into a spatial filter. This approach requires physically changing the filters for different substrates and is impractical for current manufacturing processes. A third method uses a spatial filter consisting of mechanically linked bars positioned to block the diffracted light (see, U.S. Pat. No. 5,742,42 to Drake). This approach is limited by its resolution. A fourth method uses a micro-mirror array as a spatial separator to direct different components of the diffraction pattern to different detectors (see, U.S. Pat. No. 5,506,676 to Hendler). This approach requires multiple photo-detector subassemblies of varying sensitivity and is costly to implement.

Further, care must be exercised to ensure that the intensity of the scattered light from the working surface does not exceed the designed detection limits of the detector (i.e., saturate the detector). Otherwise, when the detector is saturated, it would no longer be able to distinguish between two different surface conditions. The sensitivity of the detector may be reduced to accommodate detection of a wider range of intensities, but that would mean that the apparatus would be less sensitive at lower intensity levels. In the alternate, the intensity of the scattered light may be reduced.

For example, a change in the collection angle relative to the illumination angle will affect the intensity of the scattered light, and hence the sensitivity of the inspection apparatus. Several methods of varying the collection angle relative to the illumination angle exist in the art. One method uses a mechanical curtain or a transparent liquid crystal light valve to progressively cut out part of the collection window, which results in changing the solid collection angle. This approach is slow and cannot be changed during mid-scan. Another approach physically raises or lowers the collection assembly or its subassembly. This approach requires precise optical realignments and is costly.

What is needed is an improved optical inspection apparatus that can dynamically and spatially attenuate the scattered light from the working surface, especially scattered light from known surface's topography, without compromising detection sensitivity.

SUMMARY OF THE INVENTION

The present invention provides a simplified, low cost, efficient, reliable and stable optical attenuator that attenuates the intensity of the scattered light from a working surface with respect to a detector. The present invention is particularly suited for deployment in an optical surface inspection apparatus for identifying unknown surface conditions of a working surface based on detection of scattered light from the surface.

In one aspect of the present invention, a dynamic spatial attenuator that is reflective in nature is deployed in the collection optics of an optical surface inspection apparatus. The attenuator is selectively controlled to vary the amount of scattered light, so as to vary the intensity of the scattered light reaching the detector. By adjusting and optimizing the intensity of the scattered light with respect to the detector, the detector can operate with an increased resolution and at the highest sensitivity possible.

In one aspect of the present invention, the dynamic spatial attenuator comprises a two-dimensional array of reflective surfaces, which may be individually controlled to divert a desired amount of scattered light away from the detector, resulting in a decrease in the intensity of the scattered light reaching the detector. In one embodiment, the reflective array comprises a two-dimensional micro-mechanical reflective array, made up of tiny moveable reflective elements. Each individually addressable element can be tilted to attenuate the scattered light that reaches to different destinations. The reflective array may be controlled to tilt the individual reflective elements to a position such that scattered light is selectively diverted to the detector by some of the reflective elements in the array (hereinafter referred to as an "on" state or fully "on" state since there is only one position in which the reflective elements divert light to the detector), and other reflective elements are diverted away from the detector (i.e., in an "off" state, with a fully "off" state in which light is diverted away from the detector and to a light dump). A desired attenuation pattern can be dynamically configured on-the-fly during the optical inspection process.

In one embodiment, by selectively controlling a predetermine number of reflective elements in the array to divert light to the photo-detector, the desired level of attenuation is achieved. In another embodiment, the desired level of attenuation is achieved by controlling the relative "on" and "off" durations in which some or all of the reflective elements are diverting light to the detector and light dump. For example, the reflective elements may be controlled to flicker at a regular cycle at a frequency that results in the desired average duration in which the reflective elements are in the fully "on" state at which light is being diverted to the detector. Because the elements are in the "off" state when light is not diverted to the detector (the elements do not need to be at the fully "off" state to divert light away from the detector), the duration of the "off" and "on" duration are therefore not equal in a regular cycle. Alternatively, the reflective elements may be controlled to alternate between "off" and "on" in an irregular cycle in a manner where the reflective element is diverting light to the detector (fully "on") at a first portion of a flicker cycle and diverting light away from the detector ("off") in a second portion of the flicker cycle, whereby the duration of the first and second portions of the cycle maybe equal for a 50% attenuation, or unequal for a less than or greater than 50% attenuation. The distribution of reflective elements that are in the "off" and "on" states (attenuation pattern) may be in a regular pattern or irregular pattern over the array. A combination of the foregoing schemes may be implemented to obtain the desired attenuation effect to prevent the detector from being saturated without compromising detection sensitivity. The reflective array may be reconfigured dynamically from one attenuation pattern to another during an optical inspection process to optimize over different areas of the working surface.

In another aspect, the reflective array may be selectively controlled to create an attenuation pattern that filters Fourier diffraction patterns created by regular surface features on the working surface.

In another embodiment, the reflective array may be controlled to vary the collection aperture (and thus the collection angle) without physically reconfiguring the detection optics to vary the collection angle relative to the illumination. By selectively turning an area of the reflective array "off" (e.g., by turning off adjacent bands of reflective elements), part of the reflective array is disabled from diverting light to the detector, thus altering the solid collection angle. The collection angle may be altered with respect to the working surface and/or with respect to the illumination angle by selectively turning "off" the rows and/or columns of the reflective array, as referenced to the working surface.

In a further aspect of the present invention, the entire micro-mechanical reflective array can be divided into sub-arrays of elements. For example, a sub-array of 100×100 elements will create a total of 10,000 reflective elements that can be turn on or off as a single unit to decrease the complexity of the controlling algorithm.

BRIEF DESCRIPTION OF THE DRAWINGS

For a fuller understanding of the nature and advantages of the invention, as well as the preferred mode of use, reference should be made to the following detailed description read in conjunction with the accompanying drawings. In the following drawings, like reference numerals designate like or similar parts throughout the drawings.

FIG. 3E is a schematic view of a configuration of the reflective elements on the reflective array superimposing two attenuation patterns to increase the effectiveness of the array; and FIG. 3F is a schematic view of a configuration of the reflective elements on the reflective array for changing the collection angle relative to the incidence beam in accordance with another embodiment of the present invention.

DETAILED DESCRIPTION OF THE PREFERRED EMBODIMENTS

This invention is described below in reference to various embodiments with reference to the figures. While this invention is described in terms of the best mode for achieving this invention's objectives, it will be appreciated by those skilled in the art that variations may be accomplished in view of these teachings without deviating from the spirit or scope of the invention.

The present invention is directed to an inspection apparatus using a dynamic reflective micro-mechanical array to detect unknown surface conditions, including desirable surface features such as traces and patterns, and undesirable surface features such as contaminants, irregularities or other defects. Once the unknown surface conditions are detected through the inspection process, further attention would be required to identify whether the particular type of surface conditions is attributed to an irregularity or from random variation of the signal. For purpose of illustrating the principles of the present invention and not its limitation, the present invention is described by reference to optical detection of a substrate for semiconductor processing. Optical detections of other types of surfaces may be implemented without departing from the scope and spirit of the present invention.

Dynamic Spatial Optical Attenuation

Figure 1:
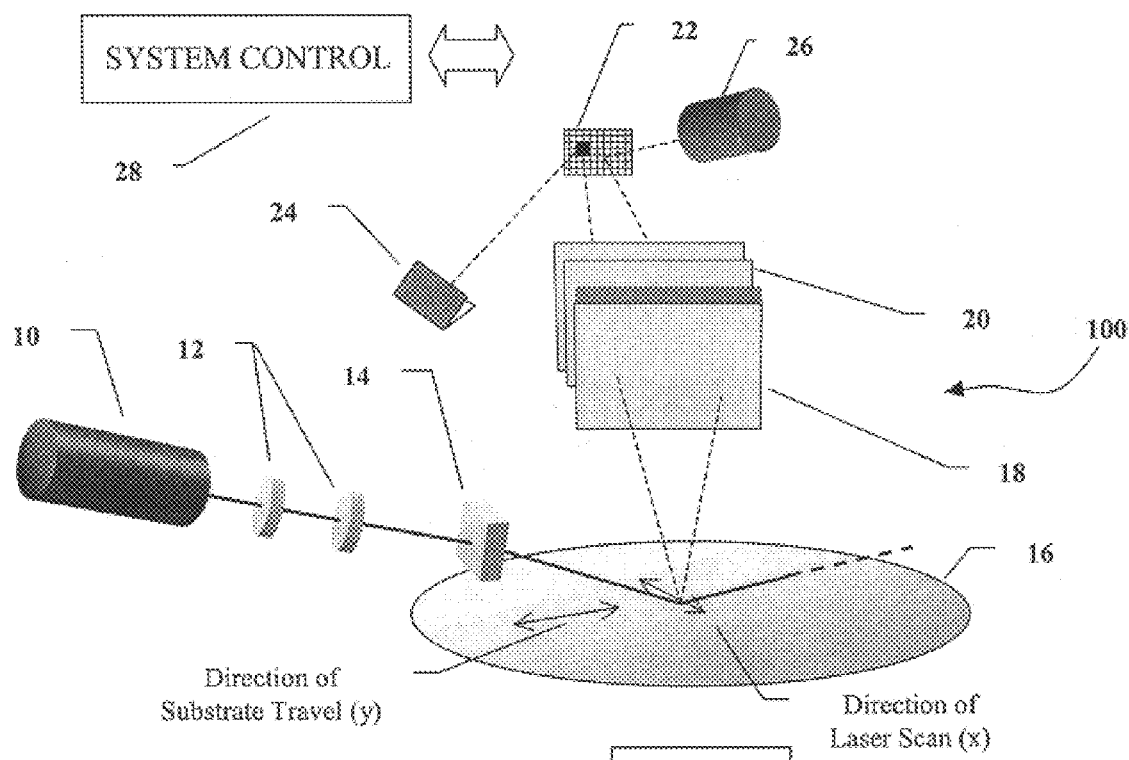
FIG. 1 is a schematic view of a optical surface inspection apparatus in accordance with one embodiment of the present invention.

FIG. 1 illustrates an inspection system with one detection assembly that uses a micro-mechanical reflective array as a dynamic spatial attenuator. A laser (10) produces a collimated beam. The laser beam is shaped and cleansed by lenses and filters (12) and is scanned by a scanning device (14) at a shallow angle onto the substrate surface (16). The substrate rests on a platform that travels along the y-axis, perpendicular to the laser scan that takes place along the x-axis, ensuring total inspection coverage. Alternatively, the inspection system can have the laser beam scanned at a higher incidence angle with multiple detection assemblies strategically placed around the hemisphere above the substrate surface.

FIG. 1 illustrates an optical inspection apparatus 100 in accordance with one embodiment of the present invention. Output light, light reflected from the substrate surface toward the photo-detector (26), generally has two destinations. When a predetermined group of reflective elements on the micro-mechanical reflective array (22) are programmed by system control (28) to turn off, they will arrange themselves to direct the unwanted deflected output light from the substrate surface (16) into the light dump (24) to be discarded, as depicted by the dashed line on the left. When reflective elements on the reflective array (22) are programmed by system control (28) to turn on, they will arrange themselves to transmit the desired scattered light, to a photo-detector (26) for additional examination, as depicted by the dashed line on the right. Detection assemblies are placed close to the scanned area to maximize the solid collection angle. Various lenses, filters, and mirrors (20) may be placed in the optical path to decrease the size of the detection assembly, focus the scattered light onto specific components, or further filter the scattered light. Once the filtered scattered light reaches the photo-detector (26), it is translated to an electrical signal and processed by computer hardware and software located within system control (28). In the present invention, the micro-mechanical reflective array (22) can attenuate the amount of scattered light from the substrate surface (16) to be diverted to the photo-detector (26) so as not to saturate the photo-detector (26) with too much light.

The control system (28) includes signal-processing capability that determines whether the signal is generated by a known pattern or an unknown surface condition. Generally, prior to the inspection process for unknown surface conditions, the inspection apparatus is first calibrated using a test surface that is defect-free with all surface conditions known to be desirable (all "known surface conditions", e.g., integrated circuit or memory patterns). The scattered light intensity profile of the test surface is mapped. During the mapping process, the apparatus "learn" the expected intensities from the scattered light at each scan spot along a scan, and optimizes its optics until the scattered light output from the reflective array (22) falls within the detection limit and an ideal level for its detection electronics. This is done in part by controlling the reflective array to define an optimized attenuation pattern for each scan spot. The reflective array is configured "off" and "on" in accordance with the further description below. The resultant (attenuated) intensity profile detected by the detector (26) is recorded as a reference intensity profile.

After the calibration process, the system is ready to inspect actual target surfaces that supposedly have similar desirable surface conditions (i.e., known surface condition). The actual scattered light pattern detected by the detector (26) is compared to a reference intensity profile for each scan location under the same inspection apparatus configuration. At each spot in the scan, the same attenuation pattern is applied by the reflective array. An unknown surface condition is present at a location if the detected intensity is different from that of the calibrated profile. The actual detected intensity is typically higher than the reference profile at a location of unknown surface condition but if the unknown surface condition absorbs light, the detected intensity will be lower. If the detection algorithm confirms that the unknown surface condition is likely caused by an irregularity, the X-Y coordinates of the laser beam's location on the substrate is recorded, allowing further processing to determine the source of the irregularity. If the surface condition is determined to be undesirable (e.g., caused by a contaminant), steps can be taken to correct the surface condition or label the component on the substrate containing the surface condition as a failed component.

Alternatively, the actual scattered light can be recorded to form an intensity map of an area of the surface. This is done using the same inspection apparatus configuration learned during the calibration process. The intensity map of the surface is compared against a reference map and an image-processing algorithm is deployed to confirm the likely source of the unknown surface condition. The reference map can be recorded during the calibration process using the defect-free surface or can be recorded during the inspection process from another part of the test surface to account for substrate-to-substrate or die-to-die variation.

Figure 5:
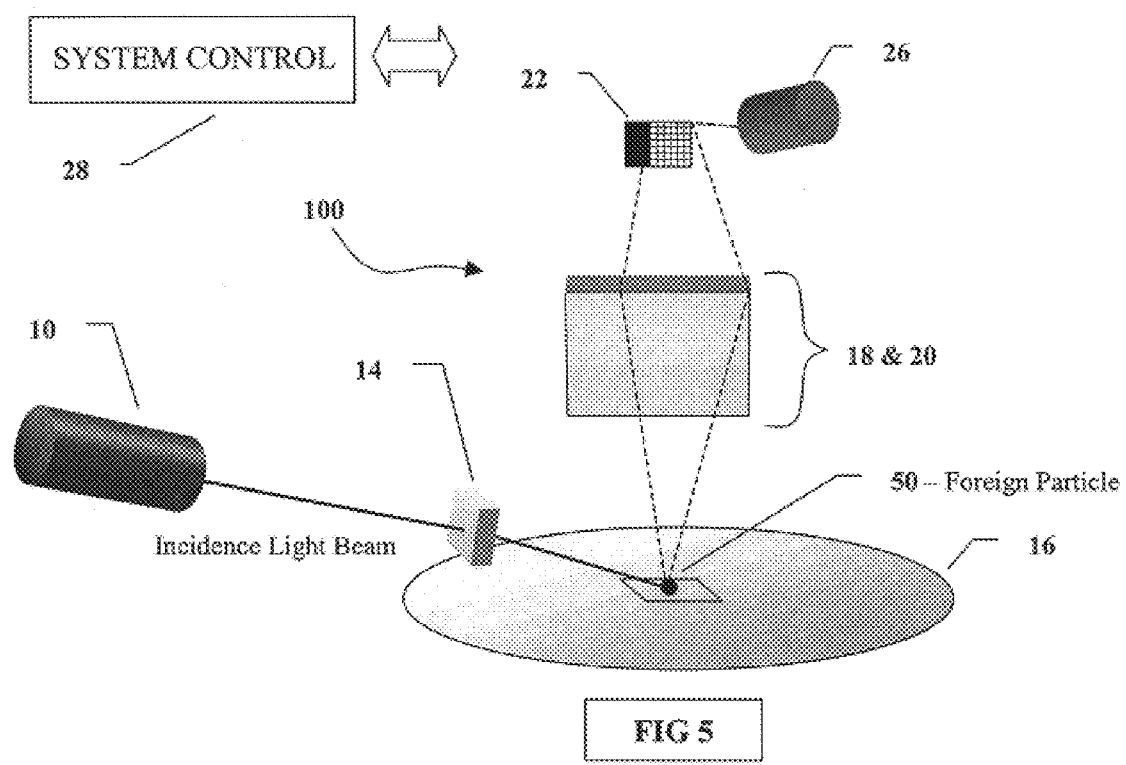
FIG. 5 is a schematic view of the inspection apparatus illustrating scanning of a target surface at a location containing a foreign particle, and the changing of the collection angle with respect to the incidence beam by configuring columns of reflective elements on the reflective array in accordance with one embodiment of the present invention.

A dynamic micro-mechanical reflective spatial attenuator aids in the inspection of non-uniformly patterned substrates, such as a semi-conductor chip as shown in FIG. 5, because the dynamic spatial attenuator can be reprogrammed during the scanning operation as scanning moves to the next point on the substrate having a different pattern. A dynamic spatial attenuator also allows rapid change to different patterns. Several spatial attenuation patterns can be stored in the memory within system control (28) to direct the orientation of each micro-mechanical reflective element in the array forming the dynamic spatial attenuator. The stored configurations can be determined from a Fourier transform calculated from recorded patterns on defect-free devices or from digitized images of Fourier transform patterns formed by Fourier transform optics.

FIG. 5 illustrates a sample memory area on a semiconductor chip containing a foreign particle (50). The scattered light from the foreign particle (50) projects toward the micro-mechanical reflective array (22) and is diverted to the photo-detector (26). The array (22) configures the reflective elements to conform to the expected intensity mapped during the calibration process. System control (28) reads the intensity of scattered light that reaches the photo-detector (26), as an electrical signal and determines whether the signal is generated by a known pattern or an unknown surface condition. If the algorithm confirms that an unknown surface condition exists, the laser beam's location on the substrate is recorded, providing the X-Y coordinates of the unknown surface condition for further determination of the nature of the condition (e.g., a contaminant).

Figure 3B:
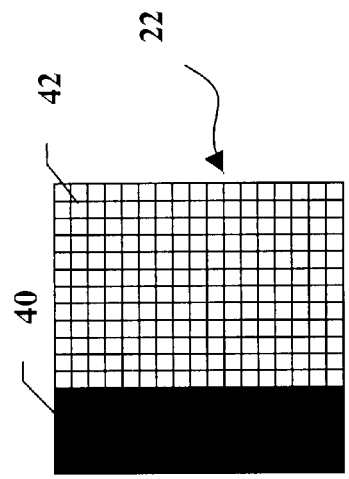
FIG. 3B is a schematic view of a configuration of the reflective elements on the reflective array for changing the collection angle relative to the incidence beam in accordance with one embodiment of the present invention.
Figure 3C:
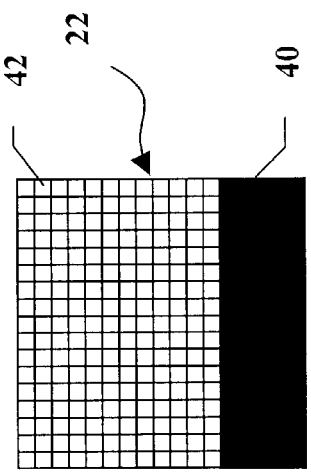
FIG. 3C is a schematic view of a configuration of the reflective elements on the reflective array for changing the collection angle relative to the substrate surface in accordance with one embodiment of the present invention.
Figure 3A:
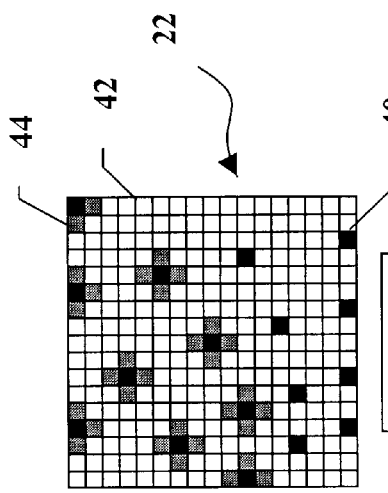
FIG. 3A is a schematic view of a configuration of the reflective elements on the reflective array for filtering a Fourier diffraction pattern in accordance with one embodiment of the present invention.
Figure 3D:
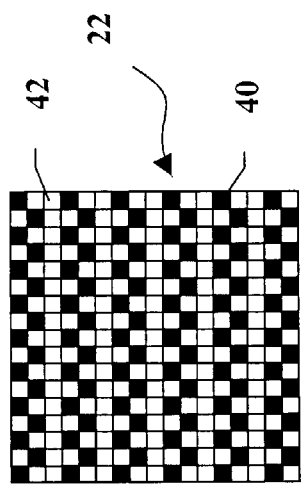
FIG. 3D is a schematic view of a configuration of the reflective elements on the reflective array for attenuating the amount of light reaching the detector in accordance with one embodiment of the present invention.

FIG. 3D illustrates how the micro-mechanical reflective array (22) can turn off approximately one-third of its reflective elements (40), deflecting the output light to the light dump (22) and turn on two-thirds of its reflective elements (42), transmitting scattered light to to the photo-detector (26). This attenuates the amount of output light reaching the photo-detector (26).

Various types of materials, such as metallized surfaces or polished surfaces may be used to achieve a reflective surface for the reflective elements on the micro-mechanical reflective array (22). The operation of the dynamic reflective spatial attenuator is programmable. An example of a controllable reflective array is the Texas Instruments' Digital Micro-mirror Device. The digital micro-mirror device is a micro-mechanical device fabricated with an array of aluminum mirrors on a layer of addressable electrodes. Each electrode can be individually activated to provide a specific force to a hinged mirror. This force rotates the mirror a given amount, and incidence light on the mirror is reflected in a direction that depends on the mirror's rotation. Individual micro-mirrors are about 25×25 $\mu$m so that a typical Fourier diffraction light could be reflected by as many as 2 million mirrors. Two million mirrors provide a high degree of control over the selected sets of Fourier components to be measured. Alternative to a micro-mechanical reflective array, a reflective liquid crystal array may be implemented to configure an array of reflective elements.

Spatial Filter for Fourier Diffractions

Figure 2:
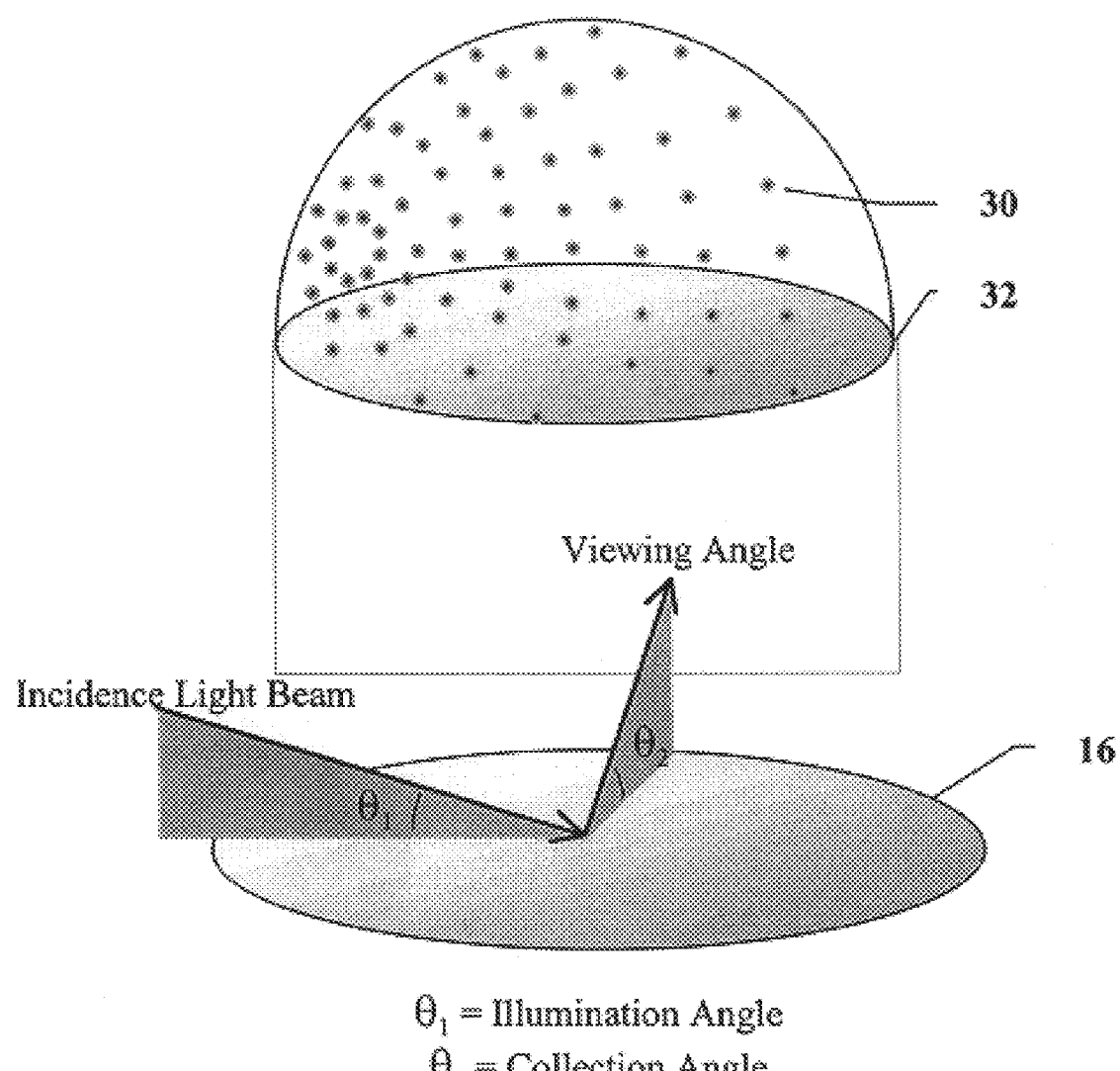
FIG. 2 is a schematic view illustrating a Fourier diffraction pattern created by a incidence light beam directed at the working surface, which is projected against a semi-opaque dome positioned above the substrate.

Regular periodic surface features (e.g., an array of cells in a memory area) produce a Fourier diffraction pattern if the incidence laser beam spot size is significantly larger than the periodic surface features. FIG. 2 illustrates how a Fourier diffraction pattern (30) is projected onto a semi-opaque dome (32) positioned above a circular substrate surface (16) as the laser beam (10) makes contact with the substrate surface (16) at an incidence or illumination angle of $\theta_1$ and reflects on of the substrate surface (16) at a scattering or collection angle of $\theta_2$. The illumination angle $\theta_1$, is the angle at which the incidence light beam is directed toward the substrate surface (16). The collection angle $\theta_2$, is the output light angle where the incidence light beam scatters off from the substrate surface (16) and is collected by the detection optics. If the laser beam's incidence angle and the periodic surface features' geometry remain constant across the substrate surface, the Fourier diffraction pattern remains stationary. Therefore, as the laser beam (10) is scanned across the memory area of the semiconductor chip, the reflected Fourier diffraction pattern (30) remains stationary. The geometry and positioning of the Fourier diffraction pattern (30) can be determined by using a Fourier transform lens or series of lenses and placing the micro-mechanical reflective array (22) at the Fourier transform plane to filter out the Fourier diffraction pattern.

FIG. 3A illustrates how the micro-mechanical reflective array (22) can arrange its reflective elements to filter the unwanted signal from a known Fourier diffraction pattern arising from a regular surface feature to the light dump (24) and direct the desired signal from scattered light to the photo-detector (26) for in depth inspection. The black squares represent reflective elements on the micro-mechanical reflective array that are turned off (40), thereby sending the deflected output light to the light dump (24). The white squares represent reflective elements on the micro-mechanical reflective array that are turned on (42), thereby sending the scattered output light to the photo-detector (26). In a further embodiment, if the switching frequency of the reflective array is fast enough, some of the reflective elements may be operated in a flicker mode. In FIG. 3A, the gray squares represent reflective elements on the micro-mechanical reflective array that alternate periodically between on and off (44), partially sending the output light to the photo-detector (26).

As mentioned above, the filtration patterns are learned by scanning a defect-free and contaminant-free specimen to learn the signal profile or map of the substrate surface (16). The system will optimize its optics for each scan spot during this learning process until the output light falls within an ideal level for its detection electronics. Individual reflective elements or groups of reflective elements on the micro-mechanical reflective array (22) are systematically turned on and off using an optimization algorithm. The changes in scattered light intensity are recorded. A memory device within system control (28) stores this learned information about the substrate surface. Combinations of filtration patterns are further refined until they allow a desirable level of scattered light to pass for further analysis without saturating the photo-detector (26). When this learning process is complete, the system is ready for inspection of actual target substrate surfaces. During inspection of an actual target substrate surface, local scattering profiles are recorded to account for variation of substrate-to-substrate or die-to-die scattering profile variation. If the scattered light differs greatly from these local ideal levels under the same conditions (e.g., attenuation and system configuration), it goes through further signal processing to verify that it is a defect and not random noise. Alternately, the signal profiles are collected to form intensity maps and this map is compared to locally produced reference intensity maps. When the system inspects target surfaces, it assumes that the current scanned section is unknown or that there might be defects present and all other sections on the substrate are known or that they are defect-free.

Collection Angle Changer

Figure 4:
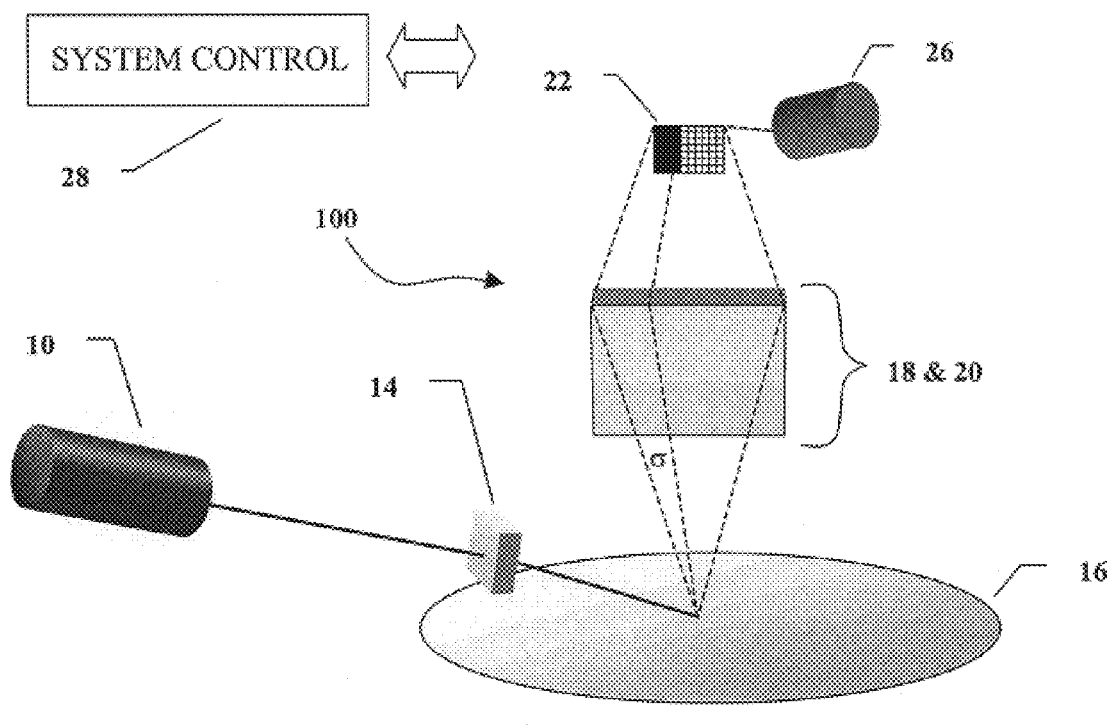
FIG. 4 is a schematic view of the inspection apparatus illustrating how the collection angle can be changed with respect to the incidence beam by configuring columns of reflective elements on the micro-mechanical reflective array in accordance with one embodiment of the present invention.

FIG. 4 illustrates how the columns of reflective elements on the micro-mechanical reflective array can be manipulated to block output light to minimize the collection angle with respect to the incidence light beam. The change in collection angle by $\sigma$ degrees corresponds to the number of columns turned on. Various lenses and components are omitted from this view for clarity.

FIG. 3B provides an enlarged representation of the micro-mechanical reflective array (22) in FIG. 4. As the independently moveable reflective elements are programmed to reduce the collection angle relative to the illumination angle by turn off a column (with reference to the substrate surface) of reflective elements, the reflective elements send only the scattered light from the reflected elements that are turned on (42) to the photo-detector.

FIG. 3C illustrates another manner in which the micro-mechanical reflective array (22) can arrange its independent reflective elements to change the collection angle. In this case, the collection angle is modified relative to the substrate surface. The bottom rows (with respect to the substrate 16) of reflective elements are turned off (40), sending the diffracted light to the light dump, thus allowing the photo-detector to absorb only the scattered light signals from the upper rows of on reflective elements (42) on the reflective array (22). FIG. 5 shows the implementation of this configuration in an inspection apparatus 100.

FIG. 3E illustrates how known attenuation patterns and other changes to the micro-mechanical reflective array can be combined to increase efficiency in contamination, irregularity or defect detection on the substrate surface (16). This figure combines FIG. 3A, depicting Fourier diffraction pattern filtration and FIG. 3C, changes in the collection angle relative to the substrate surface. The resulting signal from the on reflective elements (42) going to the photo-detector (26), in this type of combination, intensifies the signal from the perceived scattered light making detection more efficient.

FIG. 3F illustrates another manner in which the micro-mechanical reflective array (22) can arrange its independent reflective elements to change the collection angle. In this case, the collection angle is modified relative to the incidence beam. Instead of turning off a column of reflective elements, any adjacent bands of reflective elements may be turned off (40) to result in a contiguous area of reflective elements in the off state, sending the diffracted light to the light dump, thus allowing the photo-detector to absorb only the scattered light signals from the upper right corner of on reflective elements (42) on the reflective array (22).

While the present invention has been particularly shown and described with reference to the preferred embodiments, it will be understood by those skilled in the art that various changes in form and detail may be made without departing from the spirit, scope, and teaching of the invention. Accordingly, the disclosed invention is to be considered merely as illustrative and limited in scope only as specified in the appended claims.

I claim:

1. An optical surface inspection apparatus for determining the presence of unknown surface conditions on a target surface, comprising:
   illumination means for generating an incidence light beam;
   scanning means for scanning the light beam across the target surface, whereby the target surface scatters light in the presence of the light beam;
   light collection means for collecting scattered light, said light collection means comprises:
   (a) detector means for detecting light;
   (b) a dynamic reflective spatial attenuator receiving scattered light from the target surface;
   (c) control means for controlling the dynamic reflective spatial attenuator to obtain an attenuation pattern that selectively diverts light to the detector means;
   discriminating means for determining the presence of unknown surface conditions based on the light detected by the detector means.

2. The apparatus of claim 1, wherein the dynamic reflective spatial attenuator comprises an array of reflective elements.

3. The apparatus of claim 2, wherein the reflective elements are individually controllable to divert light to desired directions.

4. The apparatus of claim 3, wherein the dynamic reflective spatial attenuator comprises a micro-mechanical array of reflective elements.

5. The apparatus of claim 4, wherein the reflective elements are movable from a first position in which light is diverted to the detector means and a second position in which light is diverted away from the detector means.

6. The apparatus of claim 5, wherein the control means controls the dynamic reflective spatial attenuator in a manner such that a predetermined number of reflective elements are in the second position so as to attenuate light intensity of the scattered light from the target surface.

7. The apparatus of claim 6, wherein the control means controls the dynamic reflective spatial attenuator in a manner such that a predetermined number of the reflective elements are periodically positioned in the first and second positions.

8. The apparatus of claim 7, wherein the control means controls the reflective elements in a manner such that the reflective elements are periodically positioned in the first and second positions in regular cycles.

9. The apparatus of claim 7, wherein the control means controls the reflective elements in a manner such that the reflective elements are periodically positioned in the first and second positions in irregular cycles.

10. The apparatus of claim 6, wherein the reflective elements in the first position and the reflective elements in the second position are distributed in a regular attenuation pattern within the array.

11. The apparatus of claim 6, wherein the reflective elements in the first position and the reflective elements in the second position are distributed in an irregular attenuation pattern within the array.

12. The apparatus of claim 6, wherein the control means controls the reflective elements to distribute the reflective elements in the second position to obtain an attenuation pattern in the array to correspond to an expected Fourier diffraction pattern from the target surface, wherein Fourier diffraction is diverted away from the detector means.

13. The apparatus of claim 1, wherein the control means controls the reflective elements to obtain an attenuation pattern that filters Fourier diffraction patterns created by regular periodic surface features on the target surface.

14. The apparatus of claim 1, wherein the control means controls the reflective elements to obtain an attenuation pattern that varies collection angle of the collection optics with respect to the illumination means.

15. The apparatus of claim 14, wherein the attenuation pattern comprises of at least one band of reflective elements that is in the second position.

16. The apparatus of claim 15, wherein the attenuation pattern comprises of at least one column of reflective elements that is in the second position, with reference to the target surface.

17. The apparatus of claim 1, wherein the control means controls the reflective elements to obtain an attenuation pattern that varies collection angle of the collection optics with respect to the target surface.

18. The apparatus of claim 17, wherein the attenuation pattern comprises of rows of reflective elements that are in the second position, with reference to the target surface.

19. The apparatus of claim 3, wherein the dynamic reflective spatial attenuator comprises an array of reflective liquid crystal elements.

20. The apparatus of claim 1, wherein the light collection means further comprises a light dump, wherein the control means further controls the dynamic reflective spatial attenuator to selectively divert scattered light towards the light dump and the detector means.

21. A process of inspecting a specimen to determine the presence of unknown surface conditions on a target surface, comprising the steps:

scanning an incidence light beam across the target surface, whereby the target surface scatters light in the presence of the light beam;

collecting scattered light by applying a dynamic reflective spatial attenuator to obtain an attenuation pattern that selectively diverts light to a detector;

determining the presence of unknown surface conditions based on the light detected by the detector means.

22. A process as in claim 21, further comprising the step of calibrating the scattered light detected from a known test surface, wherein the determining step compares the light scattered from the target surface to the light scattered from the test surface.

23. A process as in claim 22, wherein the calibrating step optimizes the intensity of the scattered light from the test surface to be detected by the detector by varying the attenuation pattern.

24. A process as in claim 23, wherein the collecting step applies the same attenuation pattern as for the test surface.

25. A process as in claim 24, wherein the attenuation pattern applied at each scan spot along a scan across the target surface can vary between adjacent spots.

* * * * *